United States Patent [19]

Conkle et al.

[11] Patent Number: 4,569,235

[45] Date of Patent: Feb. 11, 1986

[54] PORTABLE, SEQUENTIAL AIR SAMPLER

[75] Inventors: James P. Conkle; Daniel Sears, both of San Antonio, Tex.; James A. Hicks, Gresham, Oreg.

[73] Assignee: The United States of America as represented by the Secretary of the Air Force, Washington, D.C.

[21] Appl. No.: 603,528

[22] Filed: Apr. 25, 1984

[51] Int. Cl.⁴ ............................................. G01N 1/24
[52] U.S. Cl. ............................. 73/863.03; 73/863.23; 73/863.12
[58] Field of Search ........... 73/863.03, 863.23, 863.11, 73/863.12, 863.31, 863.21, 863.22, 863.01, 863.02, 863.33, 864.34, 864.35, 864.63, 864.71, 864.73, 28, 170 R, 23

[56] References Cited

U.S. PATENT DOCUMENTS

| | | |
|---|---|---|
| 1,455,263 | 5/1923 | Oberfell . |
| 3,276,241 | 10/1966 | Hübner .................... 73/23 |
| 3,299,700 | 1/1967 | Stout, Jr. .................. 73/863.21 X |
| 3,395,516 | 8/1968 | Schecter et al. ............. 73/170 X |
| 3,417,605 | 12/1968 | Hahn ........................ 73/23 |
| 3,540,261 | 11/1970 | Scoggins ................... 73/863.31 X |
| 3,593,583 | 7/1971 | Anderson et al. ............ 73/863.11 |
| 3,657,920 | 4/1972 | Teel et al. ................. 73/28 |
| 3,731,539 | 5/1973 | Brittan et al. ............. 73/863.11 |
| 3,884,081 | 5/1975 | Griffith .................... 73/863.31 |
| 3,903,745 | 9/1975 | Bolser ...................... 73/863.23 X |
| 3,921,456 | 11/1975 | Newcomb, Jr. et al. ........ 73/863.02 |
| 3,965,748 | 6/1976 | Boubel et al. .............. 73/863.03 |
| 3,995,494 | 12/1976 | Muller et al. .............. 73/863.33 |
| 4,091,674 | 5/1978 | Amey ....................... 73/23 X |
| 4,170,901 | 10/1979 | Conkle et al. . |
| 4,254,657 | 3/1981 | Leichnitz et al. ........... 73/863.03 |
| 4,269,059 | 5/1981 | Baker ...................... 73/863.03 |
| 4,388,822 | 6/1983 | Heller ...................... 73/23 |
| 4,389,903 | 6/1983 | Bertone et al. ............. 73/863.23 X |

FOREIGN PATENT DOCUMENTS 398861 2/1974 U.S.S.R. ................................ 73/28

OTHER PUBLICATIONS

24-Port Sequential Air Sampler (National Environmental Instruments, Inc.) 1 page, undated.
Aeron Sequential Sampler (Precision Scientific Co.) 1 page, undated.
RAC Sequential Sampler (Research Appliance Co.) 2 pages, undated.

Primary Examiner—Stewart J. Levy
Assistant Examiner—Tom Noland
Attorney, Agent, or Firm—Donald J. Singer; Jacob N. Erlich

[57] ABSTRACT

A portable, sequential air sampler having an easily transportable housing containing therein a plurality of interrelated components which allow the air sampler to operate by either battery or "line" power as well as maintain the flow rate through the sampling media substantially constant. The components include a vacuum pump and rotary valve which are capable of sequentially drawing air through the sampling media. In addition, a flow rate control system is operably connected to the vacuum pump in order to maintain the substantially constant flow rate through the sampling media. The air sampler can vary initiation of the sampling operation from 1–999 minutes while varying the sequence of sampling from 1–99 minutes, and, yet, maintai substantially constant air flow throughout the air sampling procedure.

9 Claims, 6 Drawing Figures

Fig. 6

PORTABLE, SEQUENTIAL AIR SAMPLER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to atmospheric sampling systems, and, more particularly to a portable, sequential air sampler capable of maintaining a constant intake flow rate during the sequential air sampling operation.

An ever expanding field of study is the study and research of pollutants in the air. It is essential to continuously sample the atmosphere for the following reasons:

1. compliance with OSHA health standards;
2. compliance EPA standards;
3. as a guide in industrial air pollution;
4. to assess atmospheric quality;
5. to study jet engine combustion products;
6. to analyze and study gasoline and diesel combustion products;
7. to determine chemical contamination of water and food;
8. to study the closed environment;
9. to evaluate the atmosphere in bio-chemical experimentation;
10. chemical sampling for analysis; and
11. environmental studies during space shuttle launches.

Past air sampling systems left much to be desired since they lacked many essential qualities necessary for accurate and systematic air sampling. For example, in many instances, past air sampling systems have been incapable of being easily transported to various locations since they were dependent upon complex and extremely heavy components for their operation, and, in general required a "line" power source. In addition, those sampling systems which were battery operated and portable were not capable of being operated by a normal "line" power supply. Furthermore, the sequential testing of the atmosphere at various time intervals became a problem due to variations in flow rate encountered during the sampling operation. Consequently, a great need has arisen for a truly portable and compact air sampling instrument capable of reliable, unattended operation.

SUMMARY OF THE INVENTION

The present invention overcomes the problems encountered in the past by providing a portable, compact sequential air sampler. The air sampler of this invention is operational both on battery (DC) power or "line" (AC) power without interruption. In addition due to a novel flow rate control system, the air sampler of the present invention can reliably maintain a constant intake flow rate throughout the air sampling procedure.

The portable sequential air sampler of the present invention houses the components thereof within a compact transportable container. Easily visible upon the removal of the cover of the container is a control panel and a plurality of connectors to which air sampling impingers are connected. The portable air sampler incorporates therein a solid state control circuit having the capability of controlling a rotary valve in a preselected sequence so as to allow the air to be sampled or tested to be drawn through the plurality (preferrably 24 in number) orifices to which the air sampling impingers are connected.

The sequence of the air sampler operation of the present invention can be preset from 1 to 99 minutes. The impingers are connected by way of a plurality of connectors and the rotary valve to a servo controlled vacuum pump and a novel flow rate control system. As a result thereof, the flow rate through the impingers is capable of being maintained within 1% of a preselected value set during air sampling operation. In addition, the air sampler of the present invention has a built in delay capability so as to delay the initiation of the sampling sequence from 1 to 999 minutes. Furthermore, a number of air samplers may be interconnected in cascaded fashion and sequentially activated by a signal emanating from a preselected one of the plurality of connectors.

It is therefore an object of this invention to provide a device capable of sequentially sampling the atmosphere.

It is another object of this invention to provide a sequential air sampler which is portable and which is capable of operating both with battery power and "line" power.

It is a further object of this invention to provide a portable, sequential air sampler which is capable of maintaining flow rate through the system within 1% of a preselected flow rate setting.

It is still a further object of this invention to provide a portable, sequential air sampler which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawings and its scope to be pointed out in the appended claims.

DETAILED DESCRIPTION OF THE PREFERRED EMBODIMENT

Figure 1:
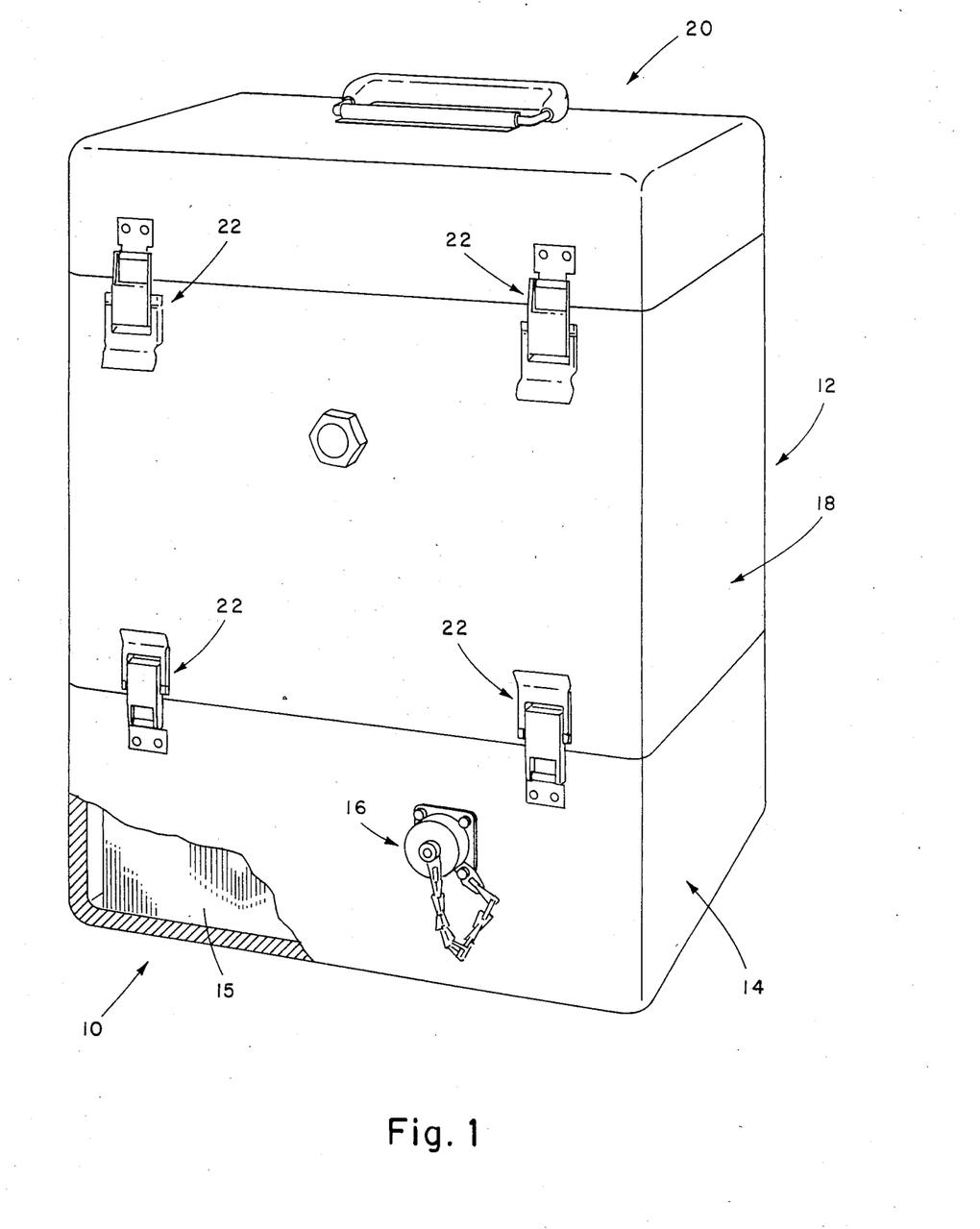
FIG. 1 is pictorial representation of the encased portable, sequential air sampler of the present invention.

Reference is now made to FIG. 1 of the drawings which pictorially illustrates the portable, sequential air sampler 10 of the present invention with its carrying case 12 depicted in the closed position to enable the air sampler 10 to be transported to any suitable area in which air sampling is to take place. As seen in FIG. 1 of the drawings, case 12 is made of three basic sections; a base 14 in which is located the battery power supply 15 and an external connector 16 to which "line" power can be operably connected; a main portion 18 which houses the major components of the air sampler 10 of the present invention and a cover 20 which protects the operational panel 21 shown in greater detail in FIG. 4 of the drawings. All of these sections 14, 18, and 20 are suitably hinged together so as to allow easy access to each and yet produce a suitable and compact unit for use in the field. Any suitable, conventional type of locking mechanisms 22 can be utilized with case 12 of the present invention in order to releasably secure the sections together.

Figure 2:
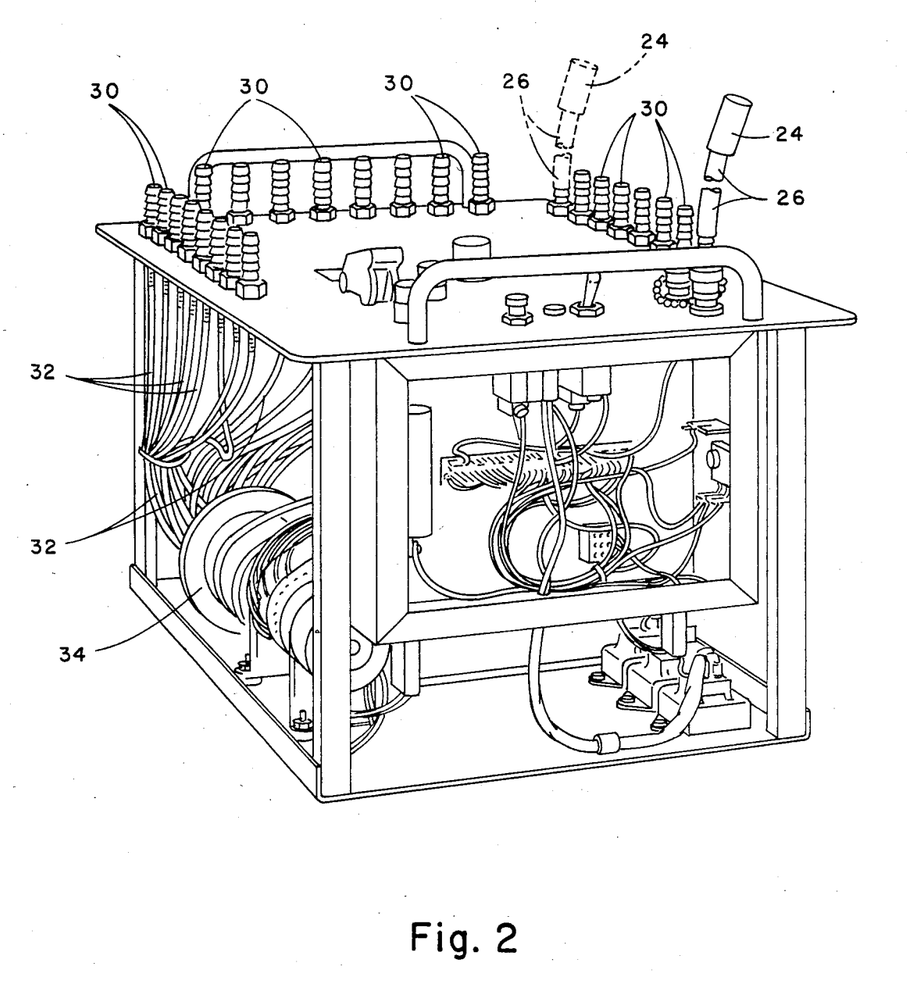
FIG. 2 is a pictorial representation of the portable, sequential air sampler of the present invention with the protective casing removed.

To better understand the air sampling system 10 of the present invention reference will now be made to FIGS. 2-4 of the drawings in which the major components of sampler 10 are clearly illustrated. As shown in these Figures the atmosphere to be sampled is drawn through a series or plurality of media samplers. These media samplers may be in the form of individual sorption tubes of the type illustrated in U.S. Pat. No. 4,170,901 or impingers of the type manufactured by the Ace Glass Co. Inc., Vineland, N.J., Catalog No. 7531-02. For illustrative purposes, the following description of the invention will utilize impingers 24 as the media samplers. Impingers 24 may be used for particulate in the air sampling, or by using various selected entrapment media and analytical techniques provide information on a wide range of airborne organic compounds in vapor phase Each of the impingers 24 is operably connected by a short length of Tygon tubing 26 to a separate one of a plurality (preferably 24in number) of impinger connectors 30 having suitably sized orifices (Although not limited thereto, the size of the orifice may by 0.020 inch) therein. The impinger connectors 30 are further interconnected by means of suitable Tygon tubing 32 (An example of which may have an internal diameter of $\frac{1}{8}$ inch and a wall thickness of 1/32 inch) to a conventional solenoid actuated rotary valve 34, shown in FIG. 2. Rotary valve 34 is preferably in the form of a commercially available Scanvalve No. 24C9121/-/55-24 manufactured by Scanvalve, San Diego, CA.

Figure 3:
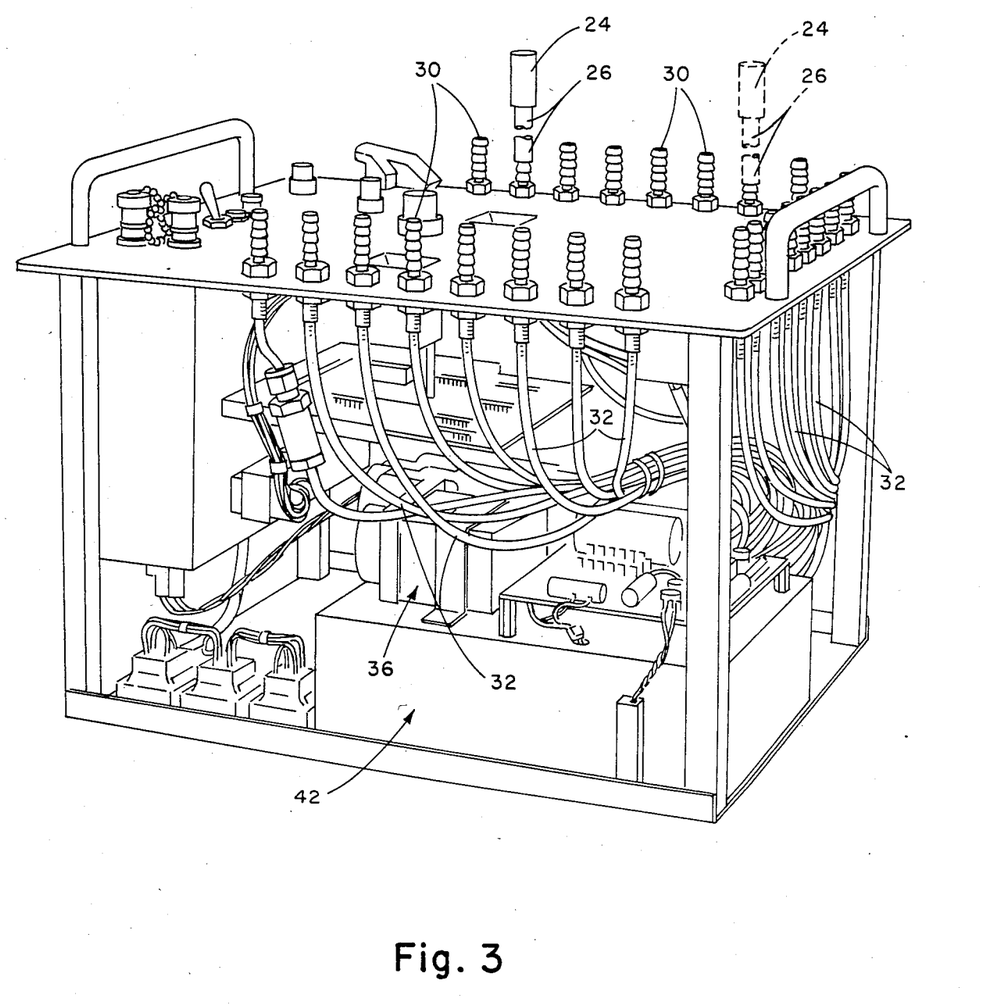
FIG. 3 is another view of a pictorial representation of the portable, sequential air sampler of the present invention with the protective casing removed.
Figure 5:
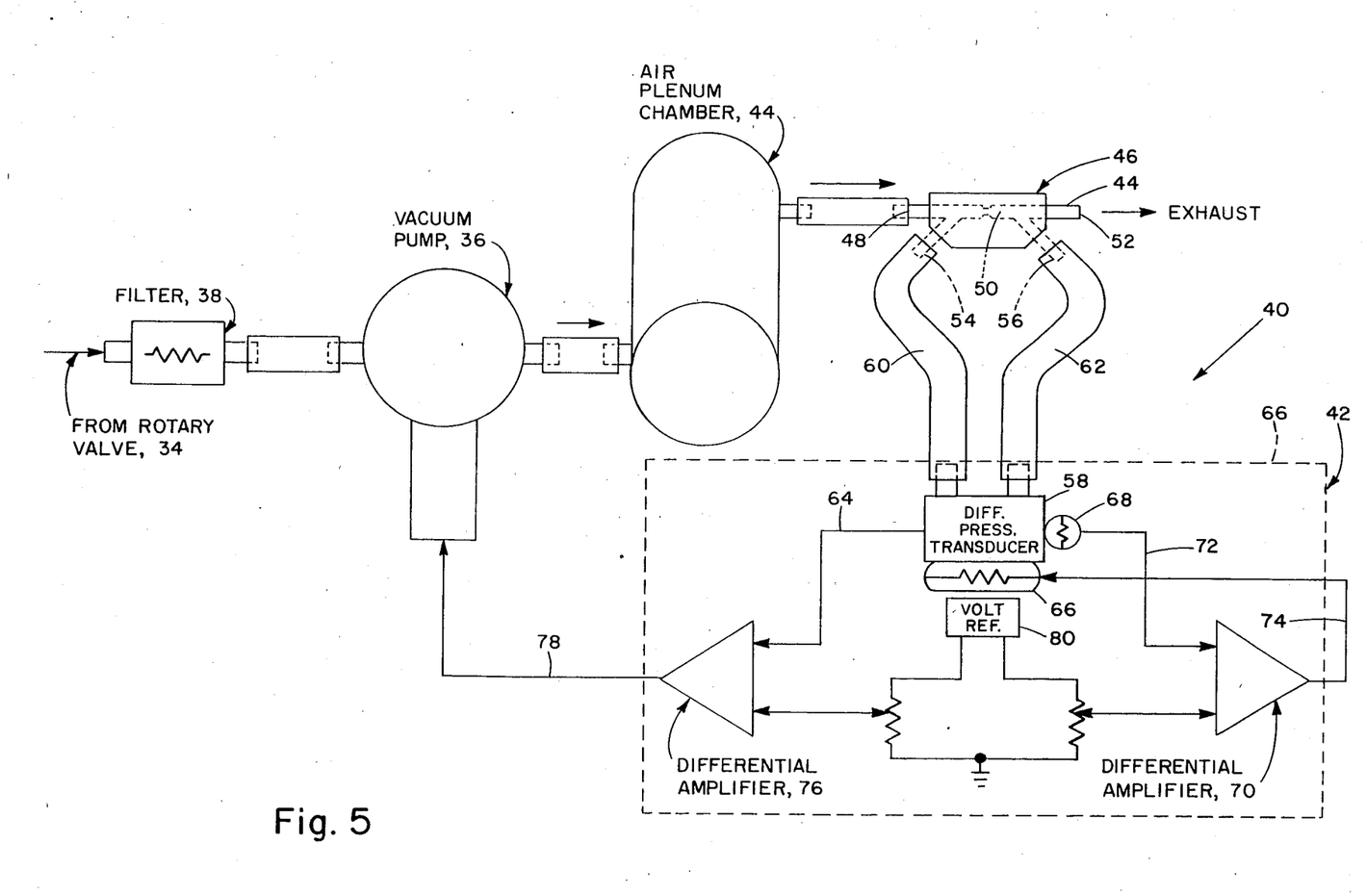
FIG. 5 is a schematic illustration of the flow rate control system of the air sampler of the present invention.

Rotary valve 34 is in turn interconnected to a servo-controlled vacuum pump 36 as shown in FIG. 3 of the drawings. More clearly illustrated in FIG. 5 of the drawings, and preferably interposed between rotary valve 34 and vacuum pump 36 is a conventional filter 38. Vacuum pump 36, illustrated schematically in FIG. 5, is controlled by means of a novel flow rate control system 40 in a manner to be described in greater detail hereinbelow. Control system 40 has a number of its elements housed within a control module 42 shown in FIGS. 3 and 5 so as to render the control system 40 insensitive to surrounding temperature and pressure changes.

As shown in FIG. 5 of the drawings, vacuum pump 36 is also interconnected to an air plenum chamber 44, utilized to dampen the pump stroke associated with vacuum pump 36, so as to provide an even flow of air through a flow sensing orifice 46 which is part of flow rate control system 40. As illustrated schematically in FIG. 5 of the drawings, flow sensing orifice 46 has four openings associated therewith. One of the openings 48 is connected to air plenum chamber 44 and is located at one end of a centrally tapered passageway 50. At the other end thereof is a second opening 52, the exhaust opening. The other two openings 54 and 56 are taps situated prior to and immediately after the tapered passageway 50 in order to sense a difference in pressure as the flow passes through orifice 46. This pressure differential is sensed by a conventional differential pressure transducer 58 located within control module 42 in a manner described in greater detail below. Once sensed, the flow rate control system 40 is capable of regulating the operation of vacuum pump 36 so as to maintain a constant flow rate through the orifices of connectors 30.

The elements of the flow rate control system 40 contained in module 42 (preferably in the form of a brass housing) are listed as follows:

(1) a differential pressure transducer 58 preferably designated as part No. LX1601 manufactured by the Sensym Corporation. Differential pressure transducer 58 is interconnected by tubing 60 and 62 to openings 54 and 56, respectively, in order to provide an electrical output signal 64 indicative of the differential pressure associated with the air flow through the flow sensing orifice 46;

(2) a heater 66 and temperature sensor 68 located adjacent differential pressure transducer 58 in order to maintain transducer 58 at a preselected temperature, preferably 55° C. Heater 66 is controlled by means of a differential amplifier 70 which receives a signal 72 from sensor 68 and provides a regulating signal 74 to heater 66;

(3) a differential amplifier 76 which provides a flow control signal 78 to vacuum pump 36 in accordance with the signal by emanating from differential pressure transducer 58; and (4) a voltage reference 80 which is interconnected to both differential amplifiers 70 and 76.

By providing a heater 66 within control module 42 it is possible to maintain a temperature within module 42 at approximately 55° C. In so doing, the elements (listed as 1-4 above) encased within module 42 remain unaffected by external temperature or pressure changes and thereby allows for a constant air flow through impingers 24 to be maintained throughout the air sampling procedure.

The air or atmosphere to be sampled is obtained by sequentially drawing the atmosphere through impingers 24 by means of vacuum pump 36 described above. The flow rate through impingers 24 is substantially constant (that is, within 1% of the preselected flow rate).

The starting or initiation time and the time of sampling through each of the plurality of impingers 24 are regulated by a timing circuit 82 utilized within the air sampler 10 of this invention. An example of such timing control circuit 82 is shown schematically in FIG. 6 of the drawings and described with reference thereto hereinbelow. By means of timing circuit 82, rotary valve 34 can be controlled so as to provide a start time delay of up to 999 minutes. In addition, the timing circuit 82 is utilized to control or vary the actual sampling time for each of the plurality of impingers 24 from 1 to 99 minutes. The sequential operation of the rotary valve 34 which is set forth in greater detail hereinbelow enables a new sample to be taken for each passage of a time interval until a total of 23 samples have been obtained. The last position, designated by element 84 in FIGS. 4 and 6 of the drawings, of rotary valve 34 is a home position from which the sampler 10 may begin again. Furthermore, this last position 84 also provides a control signal for the utilization of other samplers in cascade fashion therewith. Since this last position 84 does not have a sample of the atmosphere drawn therethrough it can be utilized as an environment control using its analyzed value as numerical subtraction from the other (23) samples.

Figure 6:
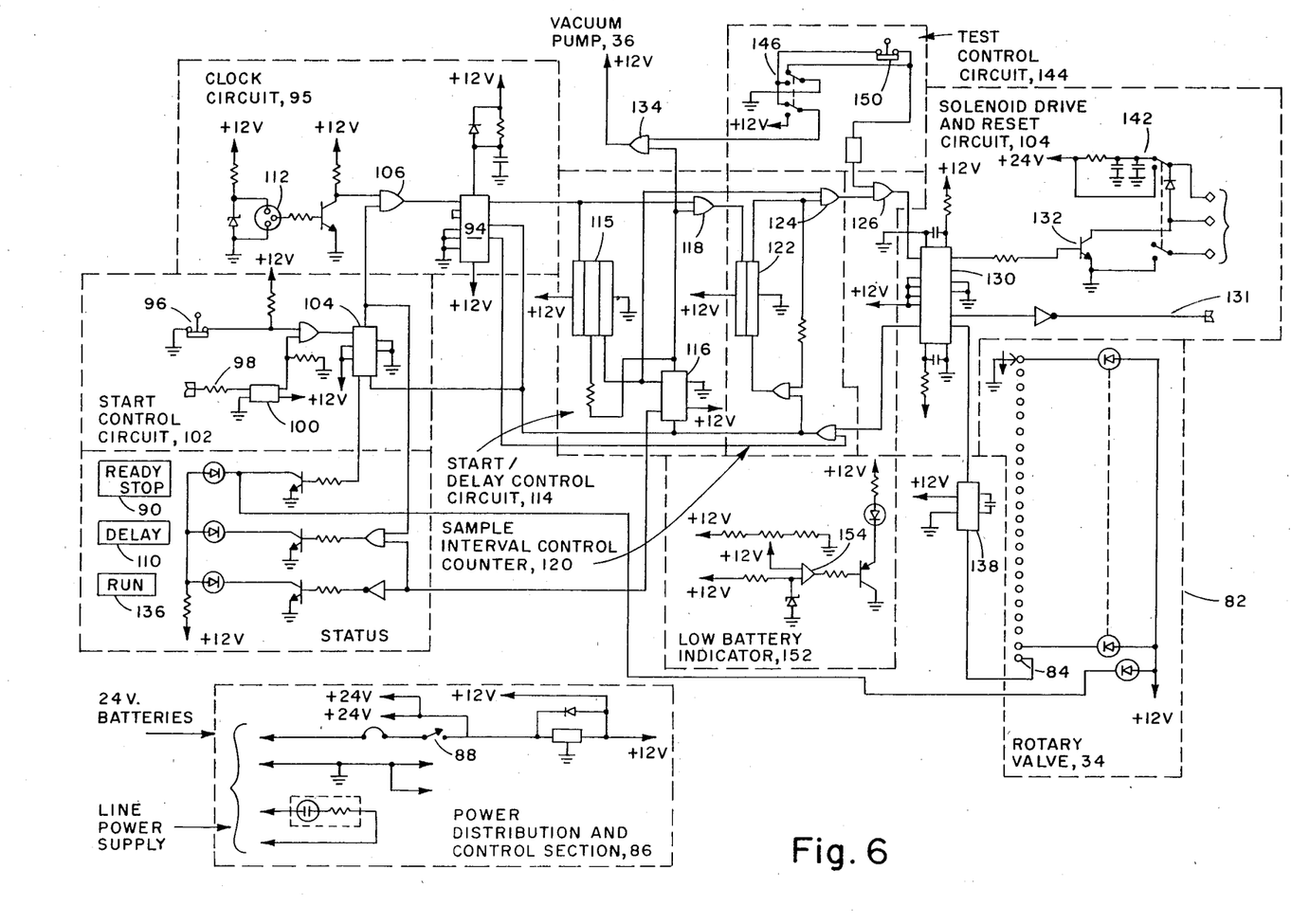
FIG. 6 is a schematic diagram of the timing control circuit of the air sampler of the present invention.

Reference is still made to FIG. 6 of the drawings for a more detailed description of a typical timing circuit 82 which can be utilized with the air sampler 10 of the present invention. Power to the timing circuit 82 is controlled by the power distribution and control section 86. When power switch 88 is turned on, 24 V DC and 12 V DC are applied to all circuits. As a result thereof, a READY-STOP status light 90 is lit on panel 92 (shown in FIG. 4), and a reset pulse is generated by a time base generator integrated circuit 94 (preferably, Motorola IC #MC14566) within clock circuit 95. Circuit 94 resets all flip-flops and counters to their initial state. When START switch 96 is actuated, or a pulse is applied to the REMOTE-START input 98 and opto isolator 100 (preferably, Litonix IC #4N35) of start control circuit 102; then flip-flop 104 (preferably, Motorola IC #MC14013) changes state, turning on gate 106 (preferably, Motorola IC #MC14081) of clock circuit 95. This acton results in turning READY-STOP status light 90 off and delay light 110 on.

The 1 Hz pulses of the Statek oscillator 112 of clock circuit 95 are fed to time base generator circuit 94 which divides the pulse into one minute pulses which are fed into the START/DELAY control circuit 114. The START/DELAY control circuit 114 is made up of three thumb switch set counters in cascade 115 (Unimax counter/timer decade switch SR-179JX3). At the end of the preselected count, that is, from 1-999 minutes, flip-flop 116 (preferably, Motorola IC #MC14013) changes state, turning on gate 118 (preferably, Motorola IC #MC14081), directing the timing pulse to a sample interval control counter 120 made up of sample interval control thumbswitch counters 122 (Unimax counter/-timer decase switch SR-179JX2), and also advancing the rotary solenoid valve 34 one position through gates 124 and 126 (preferably, Motorola IC #MC14071), and the solenoid drive and reset circuit 128 made up of a dual retriggerable,resetable monostable multivibrator 130 (preferably, Motorola IC #MC14528) and power transistor 132. Also at the same time, vacuum pump 36 is activated through gate 134 (preferably, Motorola IC #MC14071), the DELAY status light 110 goes out and the RUN indicator light 136 becomes lit.

The sample interval control counter 120 counts the one minute pulses for the preselected interval preset by the thumbswitches 122 (1-99 minutes). Upon reaching the preset count, an output pulse advances the rotary solenoid valve 34 through gates 124 and 126 and the drive circuit 128, and resets the counters for the next interval. This process will continue stepping rotary solenoid valve 34 from position to position. Upon reaching the last position 84, a pulse is developed by the contacts on the solenoid wafer switch and passed through the debounce circuit 138 (preferably, Motorola IC #MC14490) to monstable multivibrator 130 which develops a reset pulse and resets all counters and flip-flops to their initial state providing a 60 msecond pulse at STOP OUT CONNECTOR 131 turning off pump 36 and lighting the READY-STOP indicator light 90.

Figure 4:
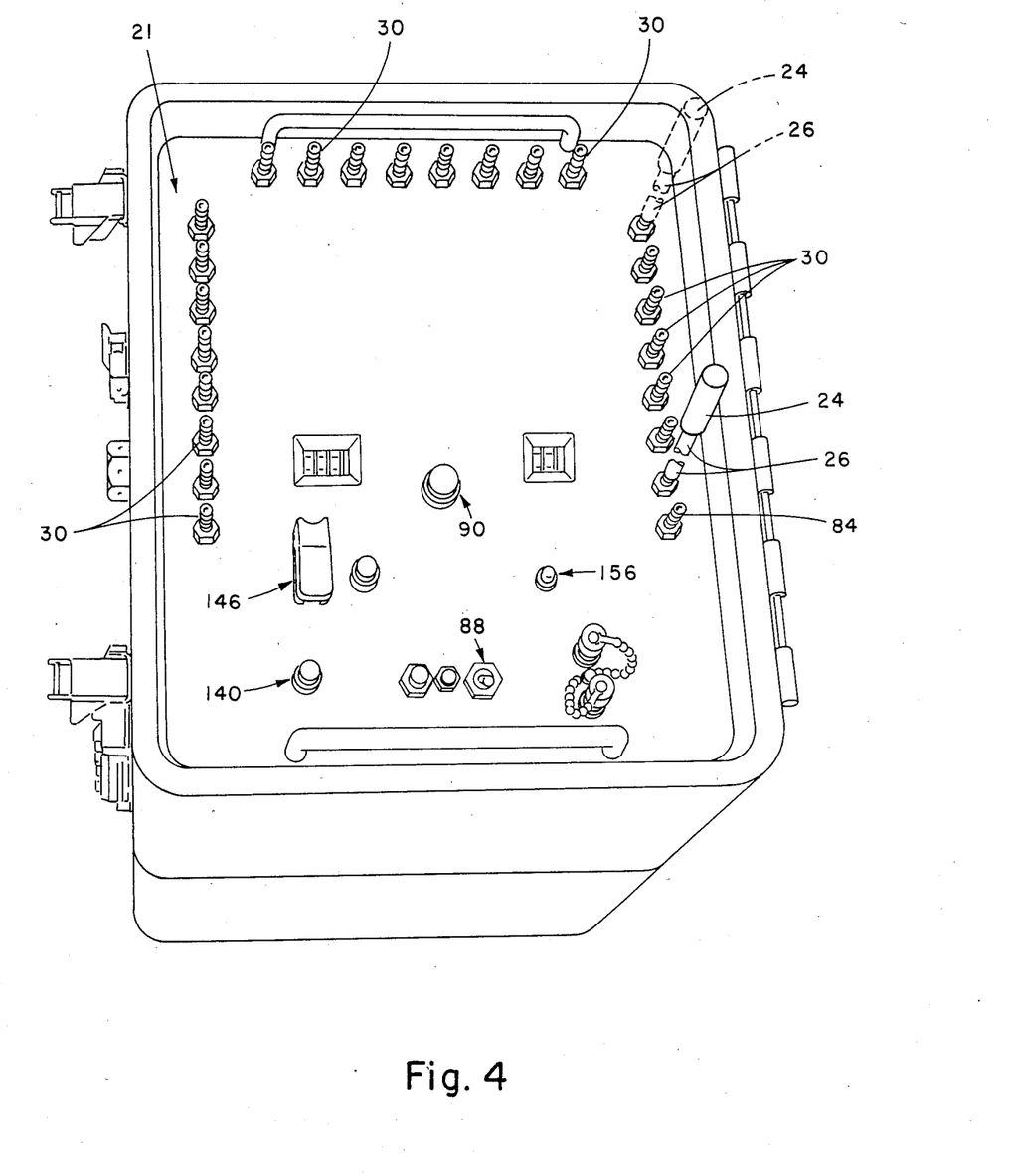
FIG. 4 is a top view of the portable, sequential air sampler of the present invention illustrating the panel.

At any time during the operation of timing circuit 82, the rotary solenoid valve 34 may be returned to the last position, 84, by merely pushing the AUTO-HOME button represented by (1) element 140 on panel 21 shown in FIG. 4 and (2) by switch 142 in circuit 82. Operational testing is provided by a TEST control circuit 144, by placing switch 146 in the test position, which activates the vacuum pump 36 through gate 134 (preferably, Motorola IC #MC14081) and allows single stepping of the rotary solenoid valve 34 by actuation of STEP switch 150. The low battery indicator circuit 152 compares the battery voltage with that from the regulated 12 volt buss in comparator 154 (preferably, National Semiconductor #LM324N), and turns on the low battery indicator 156 on panel 92 when the battery voltage drops below 19.5 volts.

MODE OF OPERATION

In order to place the air sampler 10 of this invention in operation, the battery 15 is fully charged. In this manner either battery operation (portable) or 110 V line power can be used. By utilizing line power it is possible to maintain the battery 15 in its fully charged state for use when needed. If there is a failure in the line power, via power company, electrical storm, or even accidently removing of the power cord, sampler 10 will continue to operate and the sampling scheme kept intact.

Thereafter, one merely introduces the time interval delay prior to starting and the time interval sampling period for each of the plurality of air sampling impingers 24. Power switch 88 is turned on and at least 15 minutes is allowed to pass before the sampler is initiated. This allows the temperature of the pressure transducer 58 within module 42 sufficient time to stabilize. Impingers 24 are filled with the appropriate media or sorbent samplers and the impingers are attached to connectors 30 by a short length of Tygon tubing 26.

The sample flow is arranged so that the air sample is drawn from the atmosphere through the sample media. The sampler 10 is now ready to operate after the above-mentioned 15 minutes have elapsed. Any change in control must be accomplished with the power switch 88 off and an additional 15 minutes passed before the air sampling may be undertaken.

Since it is essential to maintain constant flow through the sampler 10, the flow rate control system 40 described hereinabove becomes an essential element of sampler 10. Without constant flow rate any samples obtained are virtually worthless for purposes of analysis. During operation, air samples are taken sequentially through the plurality (preferably 23) of impingers 24. Upon completion, the sampler stops operation upon reaching position 84 at which time the sample media may be retrieved. If the sampling operation is stopped prior to position 84, it can be moved to the home or start position by depressing AUTO-HOME button 140. This is appropriate to prepare the system for resuse.

Although this invention has been described with reference to a particular embodiment, it will be understood that this invention is also capable of further and other embodiments within the spirit and scope of the appended claims.

We claim:

1. A portable, sequential air sampler, said air sampler comprising:
   a housing, said housing being made of a plurality of sections;
   means located within one of said sections for sequentially drawing air to be sampled through a plurality of individual air sampling media;
   means located in said one section operably connected to said air drawing means for maintaining the flow rate through each of said plurality of air sampling media to within approximately 1% of a preset flow rate under varying external conditions of temperature and pressure, said flow rate maintaining means including means operably connected to said air drawing means for providing a first signal indicative of flow rate change and utilizing said first signal to provide a second signal, said second signal being utilized by said air drawing means to control said air drawing means so as to maintain said flow rate through said air sampling media to within approximately 1% of said preset flow rate;

means located within another one of said sections for selectively providing either AC or DC power to said air drawing means and said flow rate maintaining means; and an accessible panel having means for interconnecting said plurality of air sampling media to said air drawing means and means to control as well as to visually indicate various stages of operation of said air sampler.

2. A portable, sequential air sampler as defined in claim 1 wherein said flow rate maintaining means includes means for preventing said flow rate maintaining means from being adversely affected by varying external conditions of temperature and pressure, said means for preventing said flow rate maintaining means from being adversely affected by said varying external conditions including an enclosure and means within said enclosure for maintaining a constant temperature therein.

3. A portable, sequential air sampler as defined in claim 1 wherein said housing is in the form of a carrying case, said carrying case including a cover which is removable to expose said panel.

4. A portable, sequential air sampler as defined in claim 1 wherein said air drawing means comprises a vacuum pump, a rotary valve operably connected to said vacuum pump and means for controlling said rotary valve, said controlling means establishing the starting time of said rotary valve and the length of time said rotary valve maintains said flow rate through each of said air sampling media thereby establishing the sequence of air to be drawn through said plurality of air sampling media.

5. A portable, sequential air sampler as defined in claim 4 wherein said air drawing means further comprises means interconnected between said vacuum pump and said flow rate maintaining means for dampening the pump stroke associated with said vacuum pump.

6. A portable, sequential air sampler as defined in claim 5 wherein said flow rate maintaining means includes means for preventing said flow rate maintaining means for being adversely affected by varying external conditions of temperature and pressure, said means for preventing said flow rate maintaining means from being adversely affected by said varying external conditions including an enclosure and means within said enclosure for maintaining a constant temperature therein.

7. A portable, sequential air sampler as defined in claim 6 wherein said housing is in the form of a carrying case, said carrying case including a cover which is removable to expose said panel.

8. A portable, sequential air sampler as defined in claim 7 wherein said means for providing said first signal comprises a flow sensing orifice operably connected to said vacuum pump, and means for sensing a pressure difference as said flow passes through said flow sensing orifice, said pressure difference being indicative of a change in flow rate.

9. A portable, sequential air sampler as defined in claim 8 wherein said means for providing said second signal comprises a differential amplifier electrically connected between said means for sensing said pressure difference and said vacuum pump.

* * * * *